(12) United States Patent
     Top

(10) Patent No.:     US 12,636,364 B2
(45) Date of Patent:      May 26, 2026

(54) ARRANGEMENT FOR VAPORIZING NANOAGENTS SUITABLE FOR THERAPY INSIDE THE HUMAN BODY AND DEVICE COMPRISING THE ARRANGEMENT

(71) Applicant: ASELSAN ELEKTRONIK SANAYI VE TICARET ANONIM SIRKETI, Ankara (TR)

(72) Inventor: Can Baris Top, Ankara (TR)

(73) Assignee: ASELSAN ELEKTRONIK SANAYI VE TICARET ANONIM SIRKETI, Ankara (TR)

( * ) Notice: Subject to any disclaimer, the term of this patent is extended or adjusted under 35 U.S.C. 154(b) by 114 days.

(21) Appl. No.: 18/571,279

(22) PCT Filed: Jun. 16, 2022

(86) PCT No.: PCT/TR2022/050599
     § 371 (c)(1),
     (2) Date: Dec. 18, 2023

(87) PCT Pub. No.: WO2022/265611
     PCT Pub. Date: Dec. 22, 2022

(65) Prior Publication Data
     US 2024/0285763 A1     Aug. 29, 2024

(30) Foreign Application Priority Data
     Jun. 17, 2021     (TR) ................................ 2021/009884

(51) Int. Cl.
     *A61K 41/00*        (2020.01)
     *A61B 8/08*         (2006.01)
(52) U.S. Cl.
     CPC ........ *A61K 41/0028* (2013.01); *A61B 8/0833*
     (2013.01)

(58) Field of Classification Search
     None
     See application file for complete search history.

(56) References Cited

U.S. PATENT DOCUMENTS 6,514,221 B2     2/2003   Hynynen et al.
2002/0038086 A1  3/2002   Hynynen
                    (Continued)

FOREIGN PATENT DOCUMENTS

KR       20200072778 A      6/2020

OTHER PUBLICATIONS

Costas D. Arvanitis, et al., Cavitation-enhanced nonthermal ablation in deep brain targets: feasibility in a large animal model, Journal of Neurosurgery, 2016, pp. 1-23, vol. 124, No. 5.

(Continued)

*Primary Examiner* — Farouk A Bruce
(74) *Attorney, Agent, or Firm* — Bayramoglu Law Offices LLC

(57)                    ABSTRACT

An arrangement and a device including the arrangement allow nanoagents that have therapeutic or diagnostic or both therapeutic and diagnostic effects to be vaporized in a specific target area in the human body. The arrangement includes at least one primary magnetic element configured to generate a first magnetic field in a first direction, at least one secondary magnetic element configured to generate a second magnetic field substantially opposite to the first direction, at least one tertiary magnetic element configured to generate a time-varying magnetic field to excite magnetic nanoparticles located in a magnetic field-free region where the opposite first magnetic field and the second magnetic field suppress each other's effects, at least one receiving coil configured to measure the magnetization of magnetic nanoparticles, and at least one first ultrasound transducer configured to apply (Continued)

ultrasound energy by providing acoustic waves onto the nanoagents located in the magnetic field-free region.

19 Claims, 4 Drawing Sheets

(56) References Cited

U.S. PATENT DOCUMENTS

| | | | |
|---|---|---|---|
| 2005/0090732 A1 | 4/2005 | Ivkov et al. | |
| 2006/0241391 A1* | 10/2006 | Rabinovitz | A61B 5/42 |
| | | | 600/420 |
| 2008/0309330 A1* | 12/2008 | Ohyu | A61B 5/05 |
| | | | 324/232 |
| 2013/0020418 A1 | 1/2013 | Machi et al. | |
| 2015/0080710 A1* | 3/2015 | Henkel | A61B 34/20 |
| | | | 600/407 |
| 2015/0231282 A1 | 8/2015 | Pozzo et al. | |
| 2020/0282055 A1* | 9/2020 | Barnsley | A61K 9/0009 |
| 2021/0106841 A1 | 4/2021 | Jiang et al. | |

OTHER PUBLICATIONS

Sayan Mullick Chowdhury, et al., Ultrasound and microbubble mediated therapeutic delivery: Underlying mechanisms and future outlook, Journal of Controlled Release, 2019.

\* cited by examiner

ARRANGEMENT FOR VAPORIZING NANOAGENTS SUITABLE FOR THERAPY INSIDE THE HUMAN BODY AND DEVICE COMPRISING THE ARRANGEMENT

CROSS REFERENCE TO THE RELATED APPLICATIONS

This application is the national phase entry of International Application No. PCT/TR2022/050599, filed on Jun. 16, 2022, which is based upon and claims priority to Turkish Patent Application No. 2021/009884, filed on Jun. 17, 2021, the entire contents of which are incorporated herein by reference.

TECHNICAL FIELD

This invention relates to an arrangement and a device comprising this arrangement that allows nanoagents that have therapeutic or diagnostic or both therapeutic and therapeutic and therapeutic and therapeutic effects to be vaporized in a specific target region in the human body.

BACKGROUND

The development of micro- and nano-scale theranostic (therapeutic and diagnostic) agents provides a personalized platform to treat various diseases at the microbiological/cellular level and to monitor the outcome of treatment. For example, cancer cells can be targeted using drug-loaded nanoparticles with antibodies that recognize overexpression of cancer-related factors.

Nanoparticles can provide drug release by responding to stimuli such as pH, temperature, light, pressure, and they can also be used for hyperthermia treatment. Ideally, theranostic agents should be effective only in the diseased region (e.g., tumor) inside the body and should not damage healthy tissue. Monitoring the drug dosage applied to the diseased region during the treatment also increases the effectiveness of the treatment.

Microbubbles are gas-filled micro-scale particles that can undergo volumetric changes under ultrasound pressure waves (acoustic waves). Since these particles effectively scatterer the ultrasound signal, they have been used as contrast agents for high contrast imaging of vessels for ultrasound imaging. The volumetric expansion and contraction (cavitation) of the microbubbles widens the spaces between the endothelial cells in the capillaries and opens the blood-organ barrier. An example of an application of this is the temporary opening of the blood-brain barrier, a structure around the capillaries of the brain that protects the brain by preventing the passage of large molecules. Said blood-brain barrier may hinder the transport of therapeutic agents and drugs to the brain in the treatment of brain diseases. As explained in the United States patent document numbered U.S. Pat. No. 6,514,221, which is the state of the art, ultrasound energy can be applied to a region with microbubbles inside the body, and open the blood-organ barrier for extravasation of therapeutic agents. The contraction and expansion of microbubbles without damaging their integrity is called stable cavitation. In cases, where the applied ultrasound power is relatively high, microbubbles may expand and collapse violently. In this case, the temperature rises extremely inside a very small volume, a high energy is released, and free radicals are generated. This phenomenon is called inertial cavitation. In order to open the blood-brain barrier by using microbubbles, stable cavitation must be provided by applying high enough ultrasound energy, while the absolute pressure of the applied acoustic waves must be kept below a certain threshold value in order to prevent the occurrence of inertial cavitation. In order to achieve this, the cavitation activity is constantly monitored, for example, by means of acoustic sensors, and when inertial cavitation formation is detected during this monitoring process, the ultrasound energy applied to the microbubbles, in other words the absolute pressure of the acoustic waves, is reduced. The inertial cavitation threshold (ultrasound power required for inertial cavitation), which depends on the absolute pressure of the applied acoustic waves, decreases with ultrasound frequency. Since the ultrasound attenuation through the skull increases with frequency, intracranial ultrasound applications can be performed at relatively low frequencies (<1 MHz). As a result, the probability of inertial cavitation in intracranial applications is relatively high. This increases the possibility of damaging healthy tissues during treatment.

In the state of the art, there are studies on the use of the mentioned inertial cavitation effect of microbubbles in therapeutic applications. For example, by inducing inertial cavitation in a diseased region inside the body, the vessels feeding the diseased cells can be damaged. In a study conducted for this purpose, the tissue was damaged by inertial cavitation of microbubbles with ultrasound energy in an area focused by ultrasound in the primate brain (C. D. Arvanitis, N. Vykhodtseva, F. Jolesz, M. Livingstone and N. MacDannold, "Cavitation-enhanced nonthermal ablation in deep brain targets: feasibility in a large animal model" J. Neurosurgery 9, 1-10 (2015)). However, tissue damage was also observed in the areas out of focus during the procedure in question, and it was also observed that the blood-brain barrier was opened. Due to these side effects, there is a need for a safer method in order to apply the mentioned procedure.

In order for the procedures briefly described above to be applied safely, it is necessary to ensure that the microbubbles are effective only in the diseased region. On the other hand, there are significant safety issues for both stable cavitation-based and inertial cavitation-based therapeutic methods in the state of the art, due to; the possibility of cavitation caused by the ultrasound energy outside the focal region of ultrasound transducer and reflections from the skull and bones, and the systemic presence of microbubbles in the vascular system.

With the rapid development of nanotechnology, the surfaces of nanoparticles can be coated with antibodies and imaging components that can bind to molecules in the diseased region. By adding elements such as drugs, viruses, nucleic acids to the nanoparticles in question, it is ensured that diseases can be treated. It is possible to sensitize nanoparticles that response to an external stimulus in order to increase their effects in targeted regions. In the state of the art, nanoagents that release their therapeutic cargo to the environment under optical, electromagnetic or acoustic energy have been suggested. Magnetic nanoparticles can be heated under a time-varying magnetic field. Antibody and drug-coated magnetic particles have been proposed in the United States patent document numbered US2005/0090732 to provide a therapeutic effect by applying a homogeneous magnetic field to a volume that encircle the diseased region. Imaging and localizing therapeutic nanoparticles or determining their concentration is important for the dosage control of the treatment. For this reason, the therapeutic nanoagents preferably should be visualized by imaging methods. Magnetic nanoparticles can be used as contrast agents in magnetic resonance imaging, and they are suitable for both therapy and imaging. In addition, accumulation of magnetic nanoparticles can be achieved in a certain desired part of the body by using an external magnetic fields.

United States patent document US2013020418 presents a type of microbubble that contain hydrophobic gas in its inside, and hydrophobic drug and lipophilic superparamagnetic nanoparticles on its surface. This microagent platform can be visualized using ultrasound because it contains gas, but it can also be visualized in magnetic resonance as it contains superparamagnetic nanoparticles. In addition, high frequency low intensity ultrasound can be applied to break up the microbubble and release the drug to the outside. However, as mentioned before, this procedure can find application in a limited region in the body due to the attenuation of the ultrasound beam, especially through hard tissues such as bones and skull.

In the state of the art, the United States patent document US2015/0231282 encloses nanobubbles containing a hydrophobic liquid such as perfluorocarbon, which can turn into gas when heated, and different types of nanoparticles such as metal, magnetic, ferroelectric, and semiconductor. Said liquid can be vaporized by using ultrasound energy and/or by increasing the temperature to increase the diameter of the bubble. This process is called acoustic droplet vaporization. Since acoustic droplet vaporization occurs relatively quickly, the therapeutic load can reach deep cells with high momentum during vaporization. Vaporized nanobubbles can be visualized using ultrasound. If the acoustic droplet vaporization process can be performed at a focused point in the tissue, it is possible to obtain the above-mentioned desired therapy effects with microbubbles without damaging the healthy tissues, since microbubbles will only be formed in the focal region of the ultrasound. On the other hand, high-frequency (>1 MHz) high-power ultrasound energy is required to achieve acoustic droplet vaporization, well above the defined safe limits for imaging. Therefore, the said high-power ultrasound energy within the tissue for acoustic droplet vaporization may cause damage to healthy tissues. In addition, as mentioned before, high frequency ultrasound cannot be applied effectively to all parts of the body (for example, the ultrasound frequency to be applied effectively in brain applications should be lower than 1 MHz). For this reason, it may not be possible to vaporize the nanobubbles in certain parts of the body, including the brain, and as a result, the desired therapy cannot be performed in the relevant regions.

SUMMARY

The aim of the present invention is to provide an arrangement and a device comprising such arrangement enabling safe vaporization of nanoagents having therapeutic or diagnostic or both therapeutic and diagnostic effects, in a focused area with low-frequency low-power acoustic waves that can pass through hard tissues such as the skull.

The arrangement enabling the vaporization of nanoagents which are introduced into the human body, preferably intravenously, having therapeutic or diagnostic or both therapeutic and diagnostic effects and comprising a volatile liquid, a core containing magnetic nanoparticles positioned inside said volatile liquid, and a surface that separates the core from the external environment by surrounding the core in order to attain the aim of the present invention, explicated in the first claim and the respective claims hereof, comprises; at least one primary magnetic element configured to create at least one first magnetic field in a first direction, at least one secondary magnetic element configured to create at least one second magnetic field in a substantially opposite direction to the first direction, at least one tertiary magnetic element configured to generate time-varying magnetic field to excite magnetic nanoparticles, at least one receiving coil configured to measure the magnetization of magnetic nanoparticles under the effect of a variable magnetic field, and at least one first ultrasound transducer configured to provide an acoustic wave at a predetermined ultrasound frequency and with an absolute pressure lower than a predetermined absolute pressure that causes inertial cavitation within the tissue at the said ultrasound frequency during vaporization of the nanoagents. Nanoagents, which provide therapeutic or diagnostic or both therapeutic and diagnostic effects by being vaporized in the human body by means of the arrangement, should remain stable in the liquid phase after they have been administered to the human body and should be able to vaporize with the energy applied to them. The boiling temperature of the liquid in the nanoagent core is relatively high in order to prevent the aforementioned nanoagents from vaporizing directly without applying any energy after they have been administered to the human body. In a preferred embodiment, perfluorocarbon is used as the liquid. Since the internal pressure of the nanoagent is greater than the atmospheric pressure by the Laplace pressure, the boiling point of the perfluorocarbon is higher inside the nanoagent than outside. The boiling point of the perfluorocarbon in a nanoagent with a diameter of 200 nm is approximately 35° C., 79° C., 117° C. and 152° C. for octafluoropropane, decafluorobutane, dodecafluoropentane and perfluorohexane, respectively. In the inventive arrangement, the first magnetic field generated by the primary magnetic element and the second magnetic field generated by the second magnetic element are almost in opposite directions to each other, so the magnetic field vanishes at a point within the human body. This point where the magnetic field is zero and its neighborhood can be called as the magnetic field-free region. Said magnetic field-free region is positioned on the diseased area to be treated during therapy. The position of the magnetic field-free region can be adjusted as desired depending on the characteristics of the first magnetic field and the second magnetic field, and the position and diameter of the magnetic field-free region can be adjusted as desired by adjusting the position of the primary magnetic element and the secondary magnetic element and/or adjusting the currents applied to the primary magnetic element and the secondary magnetic element. If the nanoagents introduced into the human body are located in the magnetic field-free region, the magnetic nanoparticles contained in said nanoagents are in a free state, in other words, they are in a position to react to another magnetic field applied from the outside. In the regions outside the magnetic field-free region, there is a magnetic field of sufficient amplitude for the magnetic nanoparticles in the nanoagents to be in magnetic saturation. Therefore, the nanoagents located outside the magnetic field-free region are not in a free state, in other words, they are not in a state to react to another magnetic field applied from the outside. Thus, when a time-varying magnetic field is generated by the tertiary magnetic element, only the magnetic nanoparticles of the nanoagents located in the magnetic field-free region can be magnetized by this time-varying magnetic field. In a preferred embodiment, a variable magnetic field with a frequency range of 100 kHz to 500 kHz is generated by the tertiary magnetic element so as to enablelocal heating of the magnetic nanoparticles, thus the core and the nanoagent. By this way, the time-varying magnetic field generated by the tertiary magnetic element contributes to the vaporization of the nanoagent in the desired region within the human body. The receiving coil of the arrangement, receives the magnetization signal formed by the time-varying magnetic field on the magnetic nanoparticles. By processing the magnetization signals received by the receiving coil, for example, by a computer, the amount and the temperature of the nanoagents in the magnetic field can be determined. The effectiveness of the therapy can also be monitored by determining the amount of nanoagents and the temperature in the magnetic field-free region. The ultrasound energy provided by the first ultrasound transducer through acoustic waves allows the nanoagents to vaporize by irradiating the cavitation core of the magnetic nanoparticles in the magnetic field-free region. In a preferred application of the invention, an ultrasound frequency with a frequency lower than 1 MHz is applied by the first ultrasound transducer, and as the ultrasound frequency is lower than 1 MHz, the targeted nanoagents can be vaporized in any desired part of the human body, since the ultrasound waves can pass through hard tissues such as the skull. By means of the arrangement according to the invention, the diameters of the nanoagents increase at high speed due to vaporization, induced both by the local heating of the nanoagents by the variable magnetic field provided by the tertiary magnetic element and by the ultrasound energy provided by the first ultrasound transducer. In this way, it is ensured that the drugs and similar therapeutic effect agents in the structures of the nanoagents are released to the environment with high momentum, thereby increasing the effect of the therapy by penetrating the therapeutic agents into the deep tissues.

BRIEF DESCRIPTION OF THE DRAWINGS

The arrangement realized to achieve the aim of the present invention and the device containing this arrangement realized to attain the aim of the present invention are illustrated in the attached figures, where.

Figure 1:
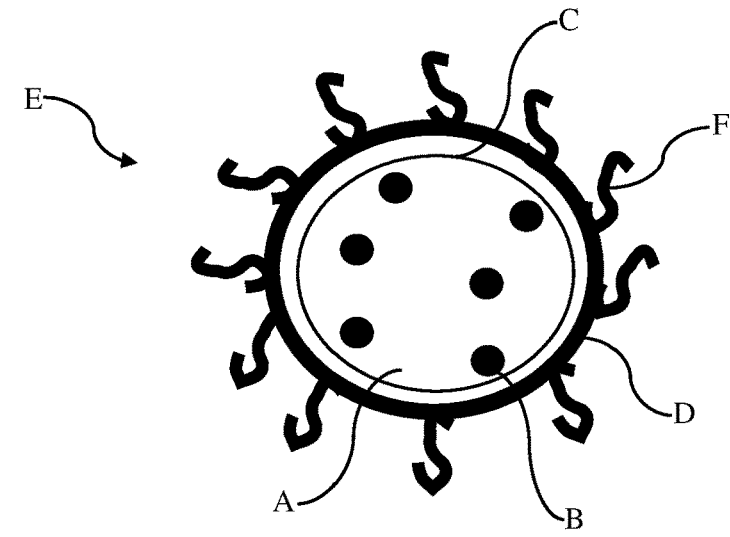
FIG. 1 is the representative view of the nanoagents to be vaporized in the human body by the inventive arrangement.

The elements illustrated in the figures are numbered individually as follows:
1. Arrangement
2. Primary magnetic element
3. Secondary magnetic element
4. Tertiary magnetic element
5. Receiving coil
6. First ultrasound transducer
7. Second ultrasound transducer
8. Coupling element 9. Control unit
10. Device
11. Body
A. Liquid
B. Magnetic nanoparticle
C. Core
D. Surface
E. Nanoagent
F. Molecule
MF1. First magnetic field
MF2. Second magnetic field
MF3. Variable magnetic field
MFFR: Magnetic field-free region
AW: Acoustic wave
V: Human body

DETAILED DESCRIPTION OF THE EMBODIMENTS

Figure 2:
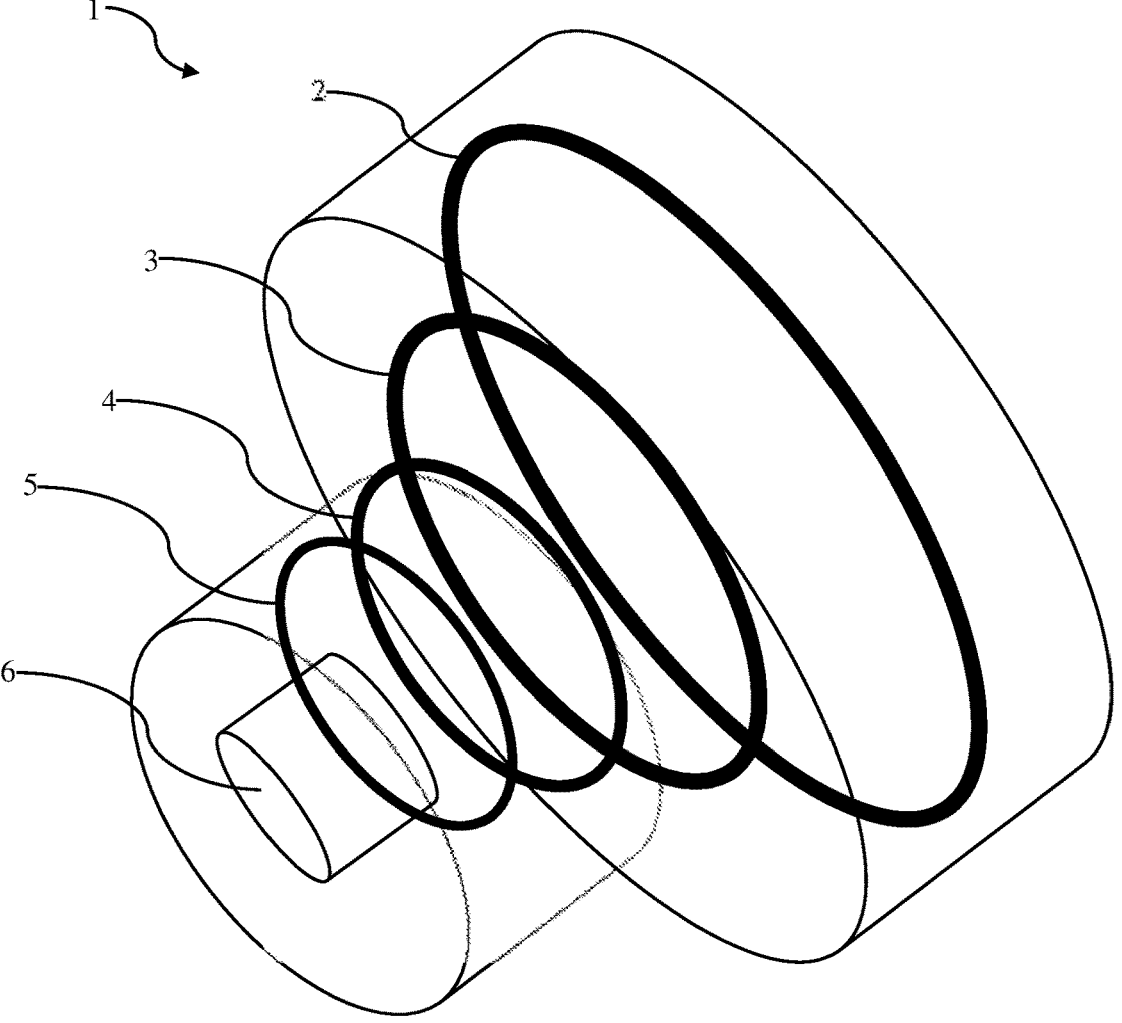
FIG. 2 is the schematic view of the inventive arrangement.
Figure 3:
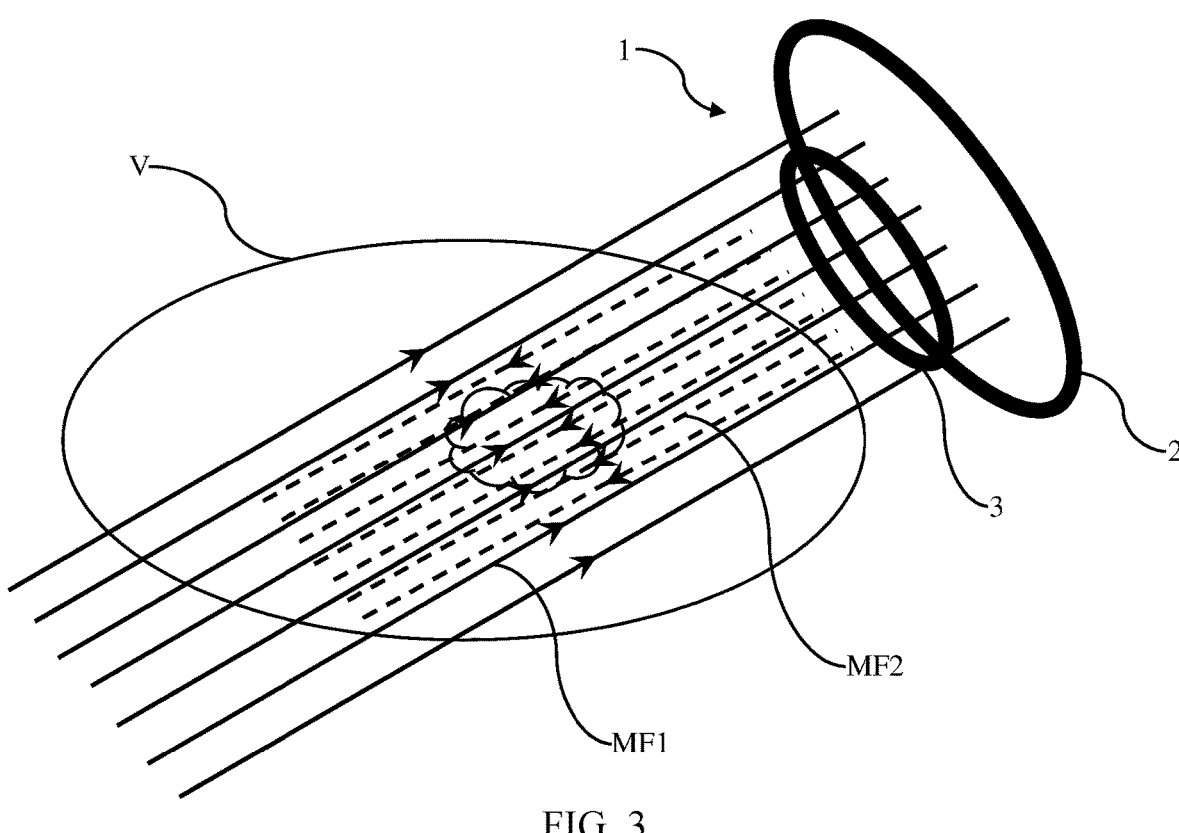
FIG. 3 is the simplified representation of the first magnetic field and the second magnetic field generated inside the human body by the inventive arrangement.
Figure 4:
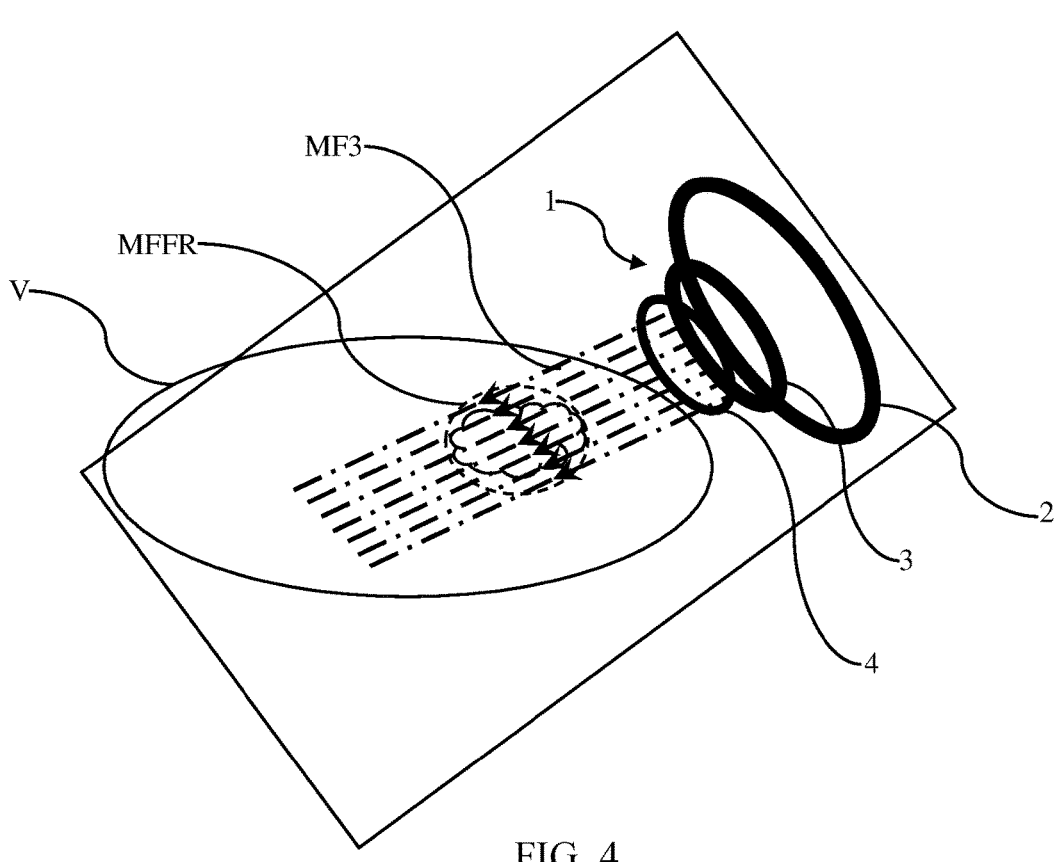
FIG. 4 is the simplified representation view of the time-varying magnetic field generated by the inventive arrangement.

An arrangement (1) allowing vaporization of nanoagents (E) previously given into the human body (V) that have a therapeutic or diagnostic or both therapeutic and diagnostic effect; wherein said nanoagents (E) include, a volatile liquid (A), a core (C) containing magnetic nanoparticles (B) inside said volatile liquid (A), and a surface (D) wrapping the core (C) to protect the core (C) from the external environment (FIG. 1) comprises; at least one primary magnetic element (2) configured to generate a first magnetic field (MF1) in a first direction, at least one secondary magnetic element (3) configured to generate a second magnetic field (MF2) substantially opposite to the first direction, at least one tertiary magnetic element (4) configured to generate a time-varying magnetic field (MF3) to excite magnetic nanoparticles (B) located in a magnetic field-free region (MFFR) where the opposite first magnetic field (MF1) and the second magnetic field (MF2) suppress each other's effects and at least one receiving coil (5) configured to measure the magnetization of magnetic nanoparticles (B) on which a time-varying magnetic field (MF3) is applied. The core (C) of the nanoagent (E) that can be vaporized in the human body (V) by means of the arrangement (1) for providing therapeutic or diagnostic or both therapeutic and diagnostic effect, contains a volatile liquid (A) and preferably contains a large number of magnetic nanoparticles (B) inside the liquid (A) (FIG. 2). Said magnetic nanoparticles (B) are preferably iron oxides having a diameter in the range of 5 nm-50 nm. In order to prevent the magnetic nanoparticles (B) from aggregating with each other and localizing in the liquid (A), the magnetic nanoparticles (B) are preferably coated with a polymer such as chitosan or another material with similar properties. The core (C) may also contain extra agents such as drugs that provide a therapeutic effect. In one embodiment, the core (C) has a diameter in the range of 10 nm to 1000 nm. The surface (D), which separates the core (C) from the external environment, encloses the core (C) in such a way that there is an air-filled space between it and the core (C) in an embodiment. The surface (D) preferably has a single or double layered phospholipid structure. In one embodiment, the surface (D) comprises at least one antibody capable of binding directly to diseased cells or to proteins present in high abundance at the site of diseased cells. The surface (D) may also contain various molecules (F) such as drugs, viruses, nucleic acids that provide therapeutic effects. Said surface (D) may contain extra magnetic nanoparticles (B) in alternative embodiments. In the arrangement (1) that allows the nanoagent (E) to be vaporized, since the first magnetic field (MF1) generated by the primary magnetic element (2)

and the second magnetic field (MF2) generated by the secondary magnetic element (3) have opposite directions, they can cancel each other's effect at some point in the human body (V). This point where the magnetic field is zero and its neighborhood can be called as the magnetic field-free region (MFFR). Said magnetic field free region (MFFR) is positioned over the diseased area to be treated. The position of the magnetic field-free region (MFFR) is determined by the properties of the first magnetic field (MF1) and the second magnetic field (MF2), and the position and diameter of the magnetic field free region (MFFR) can be adjusted appropriately by means of the currents applied to the primary magnetic element (2) and the secondary magnetic element (3). When a time-varying magnetic field (MF3) is generated by the tertiary magnetic element (4) in the magnetic field-free region (MFFR) and its neighborhood, only the magnetic nanoparticles (B) in the nanoagents (E) located in the magnetic field-free region (MFFR) become magnetized by said time-varying magnetic field (MF3). In the preferred embodiment, a time-varying magnetic field (MF3) with a frequency between 100 kHz and 500 kHz is generated by the tertiary magnetic element (4), thereby local heating of the magnetic nanoparticles (B), thus the core (C) and the nanoagent (E) can be provided. By this way, the variable magnetic field (MF3) generated by the tertiary magnetic element (4) contributes to the vaporization of the nanoagent (E) in the desired region within the human body (V). In the preferred embodiment, a variable magnetic field with a frequency range between 1 kHz and 150 kHz is also generated by the tertiary magnetic element (4), which allows the magnetic nanoparticles (B) to produce a measurable magnetization response. The receiving coil (5) of the arrangement (1) receives the magnetization response of the magnetic nanoparticles (B) to the time-varying magnetic field (MF3). By processing the magnetization signals received by the receiving coil (5), for example, by a computer, the amount of nanoagent (E) in the magnetic field-free region (MFFR) and the temperature can be calculated. The effectiveness of the therapy can be determined by calculating the amount of nanoagent (E) and the temperature in the magnetic field-free region (MFFR). While the primary magnetic element (2) and the secondary magnetic element (3) in the arrangement (1) can be selected as a permanent magnet or an electromagnet, the tertiary magnetic element (4) is preferably chosen as an electromagnet since it has to generate a time-varying magnetic field (MF3).

Figure 5:
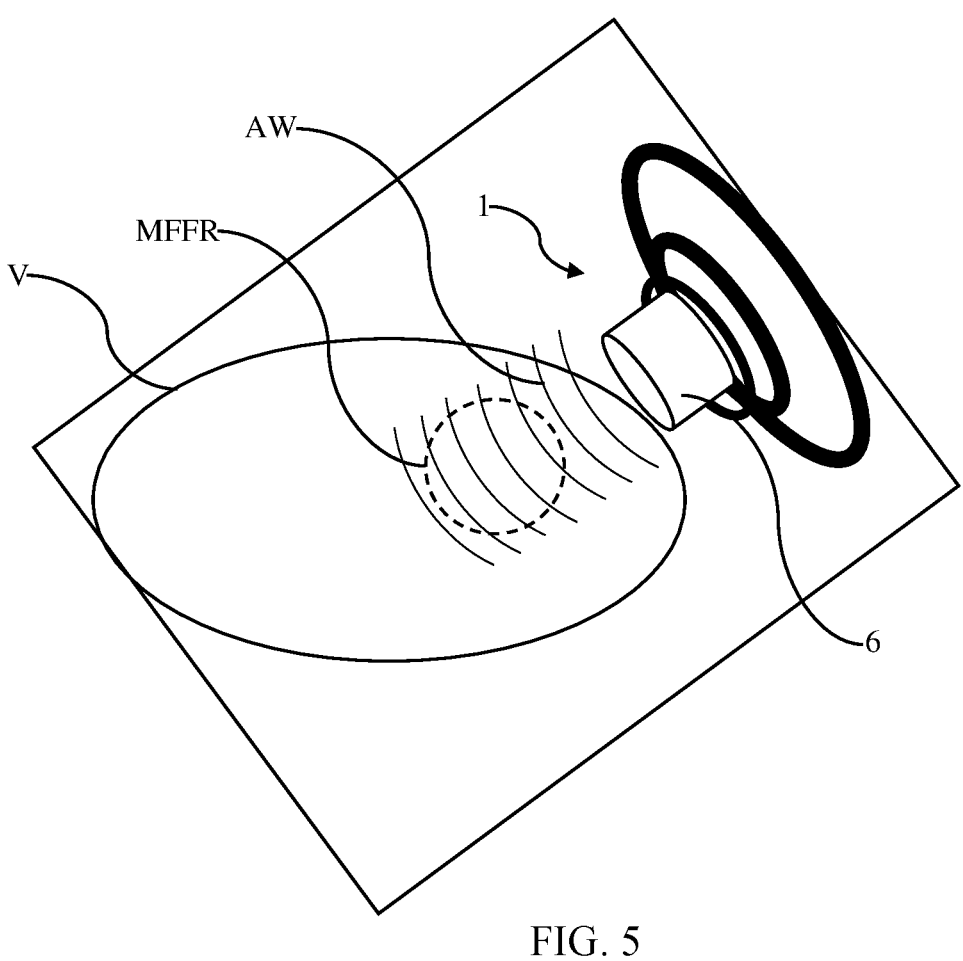
FIG. 5 is the simplified representation of the acoustic wave in the human body generated by the inventive arrangement.

The inventive arrangement (1) comprises at least one first ultrasound transducer (6) configured to provide acoustic waves (AW) at a given ultrasound frequency and with an absolute pressure lower than a predetermined minimum absolute pressure sufficient to cause inertial cavitation within the tissue at said ultrasound frequency for vaporization of nanoagents (E) (FIG. 5). By means of the arrangement (1) of the invention, the nanoagents (E) are allowed to vaporize and increase their diameter rapidly, both by local heating of the nanoagents (E) by the variable magnetic field (MF3) provided by the tertiary magnetic element (4), and also by means of the ultrasound energy provided by the first ultrasound transducer (6). In this way, it is ensured that the drugs and similar therapeutic agents in the structure of the nanoagents (E) are released into the environment with high momentum, thereby the effect of the therapy van be enhanced by the penetration of the therapeutic agents into the deep tissues. Since the acoustic waves (AW) at an absolute pressure lower than the minimum absolute pressure sufficient to put the nanoagents (E) into inertial cavitation are provided by the first ultrasound transducer (6), possible damage to the tissues by the applied ultrasound energy can be prevented during the nanoagent (E) vaporization, thereby health safety can be improved during the therapy. In addition, a stable cavitation can be induced by stimulating the vaporized nanoagents (E) with low-power ultrasound provided by the first ultrasound transducer (6). Stable cavitation opens the capillary walls and allows therapeutic agents like drugs to extravasate, and also increases the diffusion of therapeutic agents by acting as a pump. In addition to all these, stable cavitation can also weaken the diseased cells by generating heating effect in the relevant area.

In an embodiment of the invention, the first ultrasound transducer (6) can be configured to apply ultrasound energy by sending acoustic waves (AW) with a frequency of less than 1 MHz onto the nanoagents (E) located in the magnetic field-free region (MFFR). The ultrasound energy provided by the first ultrasound transducer (6) via acoustic waves (AW) generates a pressure change in the environment where the nanoagents (E) are present, allowing the nanoagents (E) to vaporize. As the frequency applied by the first ultrasound transducer (6) is lower than 1 MHz, the targeted nanoagents (E) can be vaporized in any desired part of the human body (V), even inside hard tissues such as the skull.

In an embodiment of the invention, the tertiary magnetic element (4) can be configured to generate a time-varying magnetic field (MF3) with a frequency of less than 150 kHz. In this embodiment, the variable magnetic field (MF3) at a frequency lower than 150 kHz in the magnetic field-free region (MFFR) provides magnetic relaxation of the magnetic nanoparticles (B) located in the said magnetic field-free region (MFFR). By receiving the magnetization signals of these magnetic nanoparticles (B) by the receiving coil (5), the magnetic relaxation of the said magnetic nanoparticles (B) can be measured. Accordingly, the amount of nanoagent (E) inside the magnetic field-free region (MFFR) can be measured quantitatively. Since the relaxation characteristics of magnetic nanoparticles (B) change depending on the temperature, the temperature of the nanoagents (E) in the magnetic field-free region (MFFR) and thus the temperature of the magnetic field-free region (MFFR) can be calculated at least approximately depending on the magnetization response obtained from said magnetic nanoparticles (B).

In an embodiment of the invention, the first ultrasound transducer (6) can be configured to only provide an acoustic wave (AW) with sufficient absolute pressure to put the vaporized nanoagents (E) in a state of inertial cavitation in the magnetic field-free region (MFFR). Inertial cavitation can only be achieved in the magnetic field-free region (MFFR), since the absolute ultrasound pressure required for the vaporized nanoagents (E) to enter the inertial cavitation state is much lower than the absolute ultrasound pressure required for the non-vaporized nanoagents (E) to enter the inertial cavitation state. As a result, the vaporized nanoagents (E) collapse into themselves at high speed, leading to the formation of very high temperatures locally, and the formation of free radicals by spreading the radicals in the nanoagent (E) structure to the environment. Since the said condition occurs in the diseased cell/tissue, it provides an extra therapeutic effect.

In an embodiment of the invention, the arrangement (1) further comprises at least one second ultrasound transducer (7) configured to image the vaporized nanoagents (E). By imaging the vaporized nanoagents (E), the quantitative amount of vaporized nanoagents (E) can be measured. In the embodiment of the invention in which the nanoagents (E) vaporized by means of the ultrasound energy applied by the first ultrasound transducer (6) are driven into inertial cavitation, said second ultrasound transducer (7) collects the said acoustic radiations, allowing the inertial cavitation process to be monitored, thanks to the formation of broadband acoustic radiation during inertial cavitation. By monitoring this process, the amount of nanoagents (E) undergoing inertial cavitation can be estimated, and thus the effectiveness of the therapy can be monitored and controlled instantly.

In an embodiment of the invention, the arrangement (1) also comprises at least one coupling element (8) configured to transmit acoustic waves (AW) between the first ultrasound transducer (6) and/or the second ultrasound transducer (7) and the human body (V) with low loss. The coupling element (8), can be used when the first ultrasound transducer (6) and/or the second ultrasound transducer (7) cannot make direct contact with the human body (V), and it is adapted to use a material close to the acoustic impedance of the human body (V) so as to ensure the acoustic impedance match between the first ultrasound transducer (6) and/or the second ultrasound transducer (7) and the human body (V).

Figure 6:
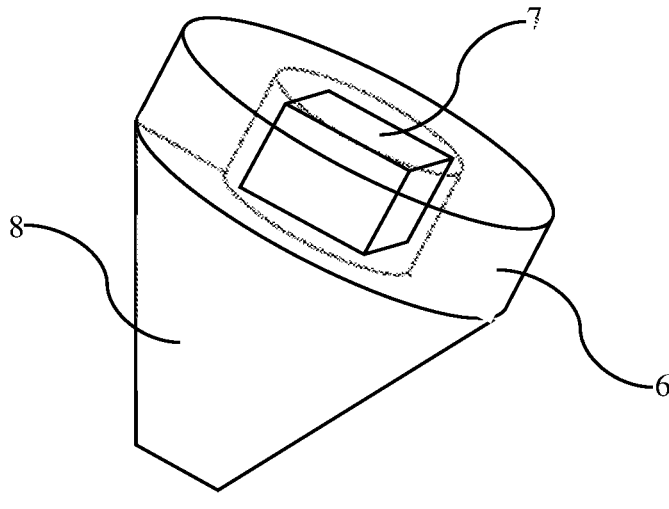
FIG. 6 is the representative perspective view of the integrated structure comprising the first ultrasound transducer, the second ultrasound transducer and the coupling element in an embodiment of the invention.

In an embodiment of the invention, the first ultrasound transducer (6), the second ultrasound transducer (7) and the coupling element (8) are arranged to have a monolithic structure by being combined with each other (FIG. 6). In this way, the production and assembly advantage is provided by reducing the number of production and assembly steps, labor and time of the assembly (1).

In an embodiment of the invention, the arrangement (1) comprises a plurality of imaging magnetic elements (not shown in the figures) configured to generate a magnetic field in two other directions orthogonal to the direction of the time-varying magnetic field (MF3) formed by the tertiary magnetic element (4), and a plurality of imaging receiving coils (not shown in the figures) configured to receive the magnetization signal of the magnetic nanoparticles (B) in these directions. In this embodiment, the magnetization signals received by the imaging receiving coils are processed, for example by a computer, so that magnetic nanoparticles (B) and thus nanoagents (E) in the magnetic field-free region (MFFR) can be visualized in two or three dimensions.

Figure 7:
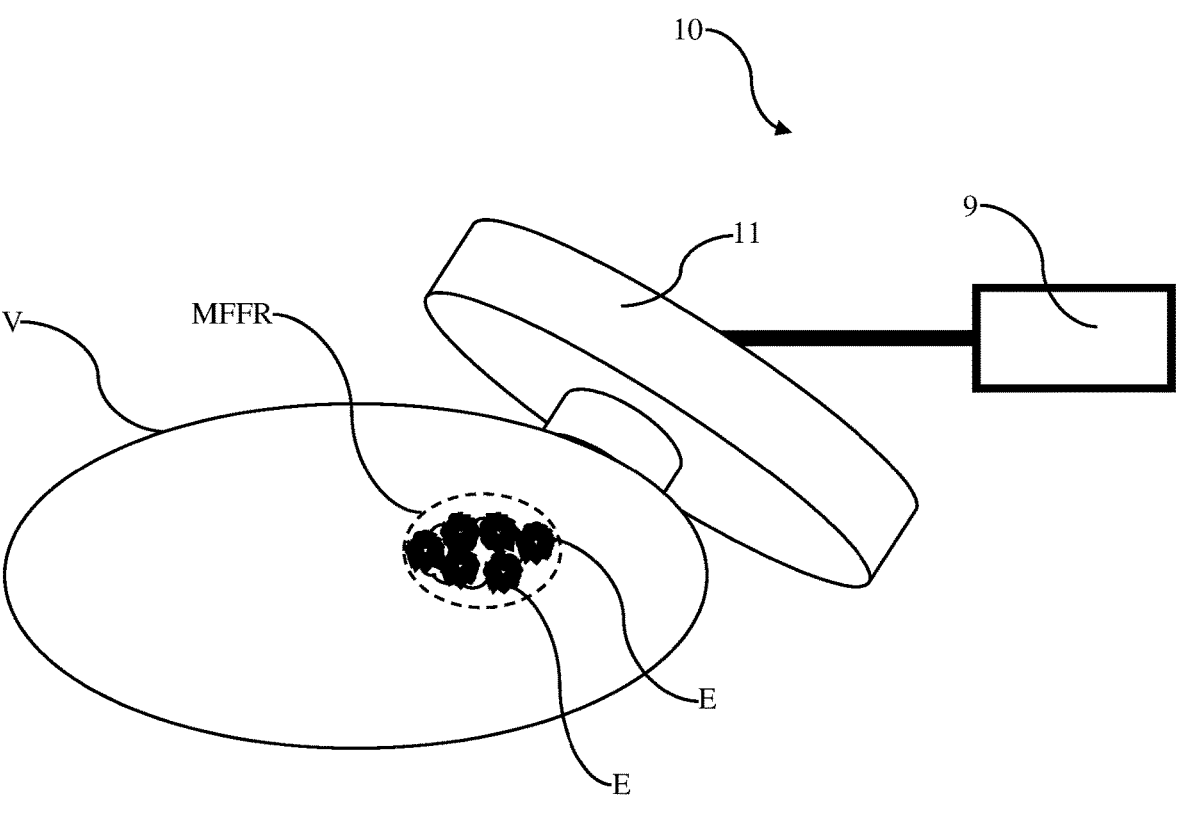
FIG. 7 is the schematic view of the device comprising the inventive arrangement.

The present invention also relates to a device (10) comprising the arrangement (1) of the above described type and at least one control unit (9) configured to drive this arrangement (1) in a controlled manner and control its operation (FIG. 7). In an embodiment of the invention, the primary magnetic element (2), the secondary magnetic element (3), the tertiary magnetic element (4), the receiving coil (5), the first ultrasound transducer (6), the second ultrasound transducer (7) and the coupling element (8) are placed inside a device body (11) that can also be named as the device head. In alternative embodiments of the invention, at least some of the elements (2, 3, 4, 5, 6, 7, 8) can be arranged to be placed around the human body (V) independently of each other. In an embodiment of the invention, the device (10) also comprises at least one first power supply and driver circuit (not shown in the figures) controlled by the control unit (9) and configured to supply the necessary current to the primary magnetic element (2) to generate the first magnetic field (MF1). In an embodiment of the invention, the device (10) also comprises at least one second power supply and driver circuit (not shown in the figures) controlled by the control unit (9) and configured to supply the required current to the secondary magnetic element (3) to generate the second magnetic field (MF2). In an embodiment of the invention, the device (10) also comprises at least one waveform generator, power amplifier and driver circuit (not shown in the figures) controlled by the control unit (9) to supply the necessary current to the tertiary magnetic element (4) to form the time-varying magnetic field (MF3). In an embodiment of the invention, the device (10) also comprises at least one acoustic wave (AW) generator, power amplifier and drive circuit (not shown in the figures) controlled by the control unit (9) configured to provide the necessary signal for the first ultrasound transducer (6) to emit the appropriate acoustic wave (AW). By controlling and driving the primary magnetic element (2) and the secondary magnetic element (3) independently of each other, it is possible to form the magnetic field-free region (MFFR) in a location suitable for therapy, in other words, in the diseased area and size in the human body (V) that needs therapy. By controlling and driving the tertiary magnetic element (4) and the first ultrasound transducer (6) independently of each other, an effective therapy is provided by adjusting the magnetic field strength and ultrasound energy to be applied for the vaporization of the nanoagents (E) located in the magnetic field-free region (MFFR) as desired. In an embodiment of the invention, the device (10) also comprises at least one sensor (not shown in the figures) configured to detect pre-defined markings in the human body (V) which can be placed in such a way as to coincide with the area where the diseased tissue is located and therefore therapy is needed. In this way, it is ensured that the magnetic field-free region (MFFR) is automatically generated at the location of the markings detected by the sensors.

This invention also relates to a method allowing the vaporization of nanoagents (E) previously given into the human body (V) that have a therapeutic or diagnostic or both therapeutic and diagnostic effect; wherein said nanoagents (E) include, a volatile liquid (A), a core (C) containing magnetic nanoparticles (B) inside said volatile liquid (A), and a surface (D) wrapping the core (C) to protect the core (C) from the external environment; wherein said method include the steps of:

generating a magnetic field free region (MFFR) on the diseased area in the human body (V) where therapy is needed, by generating a first magnetic field (MF1) and a second magnetic field (MF2), excitation and/or heating of the magnetic nanoparticles (B) within the nanoagents (E) in the magnetic field-free region (MFFR) by a time-varying magnetic field (MF3) generated specifically to spatially cover the magnetic field-free region (MFFR), vaporizing nanoagents (E) located in the magnetic field-free region (MFFR) by applying acoustic waves (AW) at a given ultrasound frequency and with an absolute pressure lower than a predetermined minimum absolute pressure sufficient to cause inertial cavitation within the tissue at said ultrasound frequency.

In the method subject to the invention; as a result of generating the first magnetic field (MF1) by the primary magnetic element (2) and the second magnetic field (MF2) by the secondary magnetic element (3), a magnetic field-free region (MFFR) is formed in a certain targeted region within the human body (V). After that, a time-varying magnetic field (MF3) is generated by the tertiary magnetic element (4), and the magnetic nanoparticles (B) of the nanoagents (E) in the magnetic field-free region (MFFR) are excited and/or heated. In addition, acoustic waves (AW) are applied by the first ultrasound transducer (6) at a certain acoustic frequency and at an absolute pressure value lower than a predetermined minimum absolute pressure sufficient to induce inertial cavitation on the nanoagents (A) at the applied frequency to vaporize the nanoagents (E) in the magnetic field-free region (MFFR). In the preferred application of the invention, the first ultrasound transducer (6) provides acoustic waves, preferably with a frequency less than 1 MHz, on the nanoagents (E) located in the magnetic field-free region (MFFR). Thanks to the application of a frequency lower than 1 MHz by the first ultrasound transducer (6), the targeted nanoagents (E) can be vaporized in any desired part of the human body (V), including tissues inside hard tissues such as the skull.

By means of the inventive arrangement (1), nanoagents (E) previously given to the human body (V) which have a therapeutic effect can be vaporized by means of acoustic waves (AW), preferably less than 1 MHz, with two different effects. The time-varying magnetic field (MF3) provided by the tertiary magnetic element (4) of the arrangement (1) at a frequency in the range of 100 kHz-500 kHz helps the nanoagents (E) to vaporize by heating the cores (C) of the nanoagents (E). Secondly, magnetic nanoparticles (B) within the nanoagent (E), especially in the core (C), act as cavitation nuclei thanks to the acoustic waves (AW) with a frequency of less than 1 MHz provided by the first ultrasound transducer (6), thereby enabling vaporization to be initiated at low ultrasound energy. Said nanoagents (E) turn into microbubbles after vaporization, and stable and inertial cavitation-based therapeutic effects are provided only in the magnetic field-free region (MFFR) generated on the diseased area in the human body (V), without being affected by the ultrasound beam. Thus, the regions outside the diseased region, in other words, regions outside the magnetic field-free region (MFFR) are not affected by the applied ultrasound energy. In addition, a stable cavitation can be induced by stimulating the vaporized nanoagents (E) with low-power ultrasound provided by the first ultrasound transducer (6). Stable cavitation opens the capillary walls and allows drug-like therapeutic agents in the vessels to get out of the vessel, and also improves the diffusion of therapeutic agents by acting as a pump. In addition to all these, stable cavitation provides a heating effect in the relevant region and allows the weakening of diseased cells.

What is claimed is:

1. A system allowing vaporization of nanoagents previously given into a human body that have a therapeutic or diagnostic or both therapeutic and diagnostic effects and having a volatile liquid, a core containing magnetic nanoparticles inside the volatile liquid, and a surface wrapping the core to protect the core from the external environment, comprising:

at least one primary magnetic element configured to generate a first magnetic field in a first direction, at least one secondary magnetic element configured to be placed on a same side with the primary magnetic element with respect to the human body and to generate a second magnetic field substantially opposite to the first direction, at least one tertiary magnetic element configured to generate a time-varying magnetic field to excite and/or heat the magnetic nanoparticles located in a magnetic field-free region where the first magnetic field and the second magnetic field suppress each other's effects, wherein the magnetic field-free region is located on a diseased region in the human body, at least one receiving coil configured to measure a magnetization of magnetic nanoparticles on which the time-varying magnetic field is applied, and at least one first ultrasound transducer configured to provide acoustic waves at a given ultrasound frequency and with an absolute pressure lower than a predetermined minimum absolute pressure sufficient to cause inertial cavitation within a tissue at an ultrasound frequency for vaporization of the nanoagents.

2. The system according to claim 1, wherein the first ultrasound transducer is configured to apply ultrasound energy by providing the acoustic waves with a frequency of less than 1 MHz onto the nanoagents located in the magnetic field-free region.

3. The system according to claim 2, wherein the tertiary magnetic element is configured to generate the time-varying magnetic field with a frequency of less than 150 kHz.

4. The system according to claim 2, wherein the tertiary magnetic element is configured to generate the time-varying magnetic field with a frequency between 100 kHz and 500 kHz.

5. The system according to claim 2, wherein the first ultrasound transducer is configured to provide an acoustic wave having sufficient absolute pressure to drive vaporized nanoagents into a state of inertial cavitation only in the magnetic field-free region.

6. The system according to claim 2, further comprising at least one second ultrasound transducer configured to image vaporized nanoagents.

7. The system according to claim 1, wherein the tertiary magnetic element is configured to generate the time-varying magnetic field with a frequency of less than 150 KHz.

8. The system according to claim 7, wherein the first ultrasound transducer is configured to provide an acoustic wave having sufficient absolute pressure to drive vaporized nanoagents into a state of inertial cavitation only in the magnetic field-free region.

9. The system according to claim 7, further comprising at least one second ultrasound transducer configured to image vaporized nanoagents.

10. The system according to claim 1, wherein the tertiary magnetic element is configured to generate the time-varying magnetic field with a frequency between 100 kHz and 500 KHz.

11. The system according to claim 10, wherein the first ultrasound transducer is configured to provide an acoustic wave having sufficient absolute pressure to drive vaporized nanoagents into a state of inertial cavitation only in the magnetic field-free region.

12. The system according to claim 10, further comprising at least one second ultrasound transducer configured to image vaporized nanoagents.

13. The system according to claim 1, wherein the first ultrasound transducer is configured to provide an acoustic wave having sufficient absolute pressure to drive vaporized nanoagents into a state of inertial cavitation only in the magnetic field-free region.

14. The system according to claim 13, further comprising at least one second ultrasound transducer configured to image vaporized nanoagents.

15. The system according to claim 1, further comprising at least one second ultrasound transducer configured to image vaporized nanoagents.

16. The system according to claim 1, further comprising at least one coupling element configured to transmit acoustic waves from the first ultrasound transducer and/or a second ultrasound transducer to the human body.

17. The system according to claim 16, further comprising a monolithic structure formed by the first ultrasound transducer, the second ultrasound transducer, and the coupling element.

18. A device comprising the system according to claim 1 and at least a control unit configured to drive the system in a controlled manner and control an operation of the system.

19. A method allowing vaporization of nanoagents previously given into a human body that have a therapeutic or diagnostic or both therapeutic and diagnostic effects and having a volatile liquid, a core containing magnetic nanoparticles inside the volatile liquid, and a surface wrapping the core to protect the core from the external environment; wherein the method comprises steps of:

generating a magnetic field-free region on a diseased region in the human body, by means of generation of a first magnetic field and a second magnetic field, wherein the first magnetic field is generated by at least one primary magnetic element, and the second magnetic field is generated by at least one secondary magnetic element placed on a same side with the primary magnetic element with respect to the human body, exciting and/or heating the magnetic nanoparticles within the nanoagents in the magnetic field-free region by a time-varying magnetic field generated specifically to cover the magnetic field-free region, vaporizing the nanoagents located in the magnetic field-free region by applying acoustic waves at a given ultrasound frequency and with an absolute pressure lower than a predetermined minimum absolute pressure sufficient to cause inertial cavitation within a tissue at the given ultrasound frequency.

* * * * *